Figure 1:
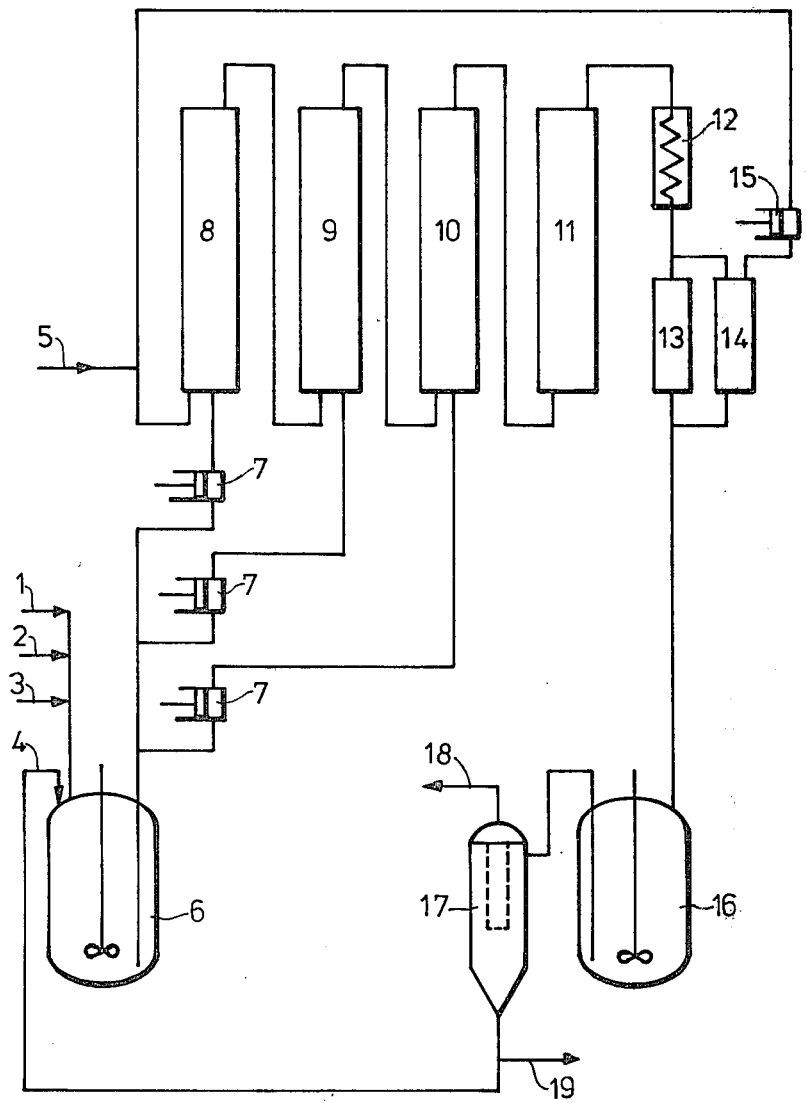

United States Patent [19]

Becker et al.

[11] 4,287,365

[45] Sep. 1, 1981

[54] REDUCTION OF AROMATIC NITRO COMPOUNDS WITH RANEY NICKEL CATALYST

[75] Inventors: Hans-Joachim Becker, Leverkusen, Fed. Rep. of Germany; Walter Schmidt, deceased, late of Leverkusen, Fed. Rep. of Germany, by Hildegard Schmidt, heiress

[73] Assignee: Bayer Aktiengesellschaft, Leverkusen, Fed. Rep. of Germany

[21] Appl. No.: 47,420

[22] Filed: Jun. 11, 1979

Related U.S. Application Data

[60] Continuation of Ser. No. 876,808, Feb. 10, 1978, abandoned, which is a division of Ser. No. 806,237, Jun. 13, 1977, abandoned.

[30] Foreign Application Priority Data

Mar. 25, 1977 [DE] Fed. Rep. of Germany ....... 2713374

[51] Int. Cl.$^3$ ............................................. C07C 85/11
[52] U.S. Cl. .................................... 564/422; 260/689; 260/690; 564/418; 564/419; 564/494; 585/270
[58] Field of Search ....................... 260/580, 689, 690; 252/466 J, 472, 477 Q

[56] References Cited

U.S. PATENT DOCUMENTS

| | | | |
|---|---|---|---|
| 3,615,215 | 10/1971 | Dohren et al. | 252/477 Q X |
| 3,673,116 | 6/1972 | Richter | 252/477 Q X |
| 4,018,835 | 4/1977 | Bizhanov et al. | 252/477 Q X |

OTHER PUBLICATIONS

Raiskina et al., "Russian Journal of Physical Chemistry", vol. 48(2), p. 285 (1974).

*Primary Examiner*—John Doll
*Attorney, Agent, or Firm*—Sprung, Felfe, Horn, Lynch & Kramer

[57] ABSTRACT

A particularly active Raney nickel catalyst is provided with a high-iron content, containing about 10 to 30% by weight of iron relative to the sum of the active metals nickel and iron. The catalyst can be prepared by treating aluminum/nickel/iron alloys which contain (1) 21 to 49.5% by weight of nickel, (2) 3 to 16.5% by weight of iron and (3) aluminum to make up to 100%, with an inorganic or organic base and separating the catalyst from the reaction mixture. According to the invention, said particularly active Raney nickel catalysts are used for the hydrogenation of organic compounds.

3 Claims, 1 Drawing Figure

REDUCTION OF AROMATIC NITRO COMPOUNDS WITH RANEY NICKEL CATALYST

This is a continuation of application Ser. No. 876,808 filed Feb. 10, 1978 (now abandoned) which in turn is a division of application Ser. No. 806,237 filed June 13, 1977 (now abandoned).

The present invention relates to a new Raney nickel catalyst with a high iron content, which is more active than Raney nickel and at the same time gives better yields as a result of a lower formation of by-products during use. Its use, particularly in the reduction of aromatic nitro compounds, for example in isopropanol/water mixtures, makes possible a considerable cost saving and improvement of the industrial process.

The preparation and use of Raney catalysts has been known for a long time and has been investigated and described many times (R. Schröter, Angewandte Chemie, 54, (1941) 229–234, 252–260; and B. M. Bogoslowski and S. S. Kosakowa, "Skelettkatalysatoren in der organischen Chemie" ("Skeleton catalysts in organic Chemistry"), VEB Deutscher Verlag Berlin (1960)). The activation of Raney catalysts by adding noble metals or their salts as well as by adding the most diverse metals to the aluminium melt has also been described (see loc. cit.). Thus, for example, the activation of Raney nickel by adding Mo, Cr and Co in amounts of 1 to 10%, relative to the nickel, has been investigated: R. Paul in Bull. soc. chim. France (5) 13, 208–211 (1946). The same additions (Cr, Mo, Co and Mn) are also described in DOS (German Published Specification) No. 2,544,761, which describes the simultaneous use of two promoters as advantageous. In addition to these metals mentioned, almost all the sub-group metals, and especially also all noble metals, are mentioned as promoters in the most diverse reactions. In most cases, the contents of foreign metals in the catalysts described are less than 10%, but most frequently less than 5%, of the nickel content.

In particular, the observations on the effect of the addition of iron, as a sub-group metal promoter, to Raney nickel are very diverse. According to Schröter (see loc. cit.) an iron content above 0.3–1% reduces the activity. A lowering in activity for the nitrobenzene reduction is also described by Z. Csurus and colleagues, CA 68, 33599j (1968), whilst J. Ishikawa, CA 54, 24471h (1960) finds an increase in activity as long as the amount added is small. According to the same author, traces of iron added during the hydrogenation of phenol—CA 55, 12701e (1961)—act as a promoter, whilst a further addition of iron reduces the activity.

It is also known (R. Paul and G. Hilly, C. r. 206, 608–610 (1938)) that no $NO_2$ and CN groups and double bonds can be hydrogenated by Raney iron alone.

A particularly active Raney nickel catalyst with a high iron content has now been found, which is characterised in that it contains about 19 to 30% by weight of iron, relative to the sum of the active metals nickel and iron, and which can be prepared by treating aluminum/nickel/iron alloys, which contain about 21 to 49.5% by weight of nickel, about 3 to 16.5% by weight of iron and aluminum, to make up to 100% by weight, with an inorganic or organic base in a manner which is in itself known.

Further, a process for the preparation of a Raney nickel catalyst with a high iron content has been found, which is characterised in that an alloy, containing about 21 to 49.5% by weight of nickel and about 3 to 16.5% by weight or iron, and aluminum to make up to 100%, is treated with an inorganic or organic base in a manner which is in itself known, a Raney nickel/iron catalyst with an iron content of about 10 to 30% by weight, relative to the sum of the metals nickel and iron, being obtained.

The catalysts according to the invention are distinguished by shorter reaction times and lower reaction temperatures and in addition produce less by-products than iron-free catalysts. Furthermore, with regard to the starting material, they are cheaper to prepare. In addition, the cost of the hydrogenation using the contact catalysts according to the invention is greatly reduced as a result of the low amount of catalyst required and because of the increased throughputs when carrying out the hydrogenation on a large industrial scale.

The latter takes effect, in particular, in the industrial production of 2,4/2,6-tolylenediamine in methanol or, in particular, in isopropanol/water mixtures, and also of phenetidine and similar amines.

Alloys with an aluminum content of about 40 to 80% by weight can be used for the preparation of catalyst according to the invention. The alloys which are customarily used contain, for example, about 45 to 70% by weight of aluminum, preferably about 50 to 60% by weight of aluminum.

The proportion of iron in the catalyst according to the invention can be about 10 to 30% by weight, preferably about 12.8 to 25% by weight and particularly preferably about 14.2 to 25% by weight, relative to the sum of the active components. In general, the alloys used for the preparation of the catalyst with an iron content of about 10 to 30% by weight contain about 21 to 49.5% by weight of nickel and about 3 to 16.5% by weight of iron, and aluminum to make up to 100% by weight. Preferably, alloys with about 22.5 to 47.5% by weight of nickel and about 7.1 to 13.7% by weight of iron, and with aluminum to make up to 100% are used, and particularly preferably alloys with about 30 to 42.5% by weight of nickel and about 7.1 to 12.5% by weight of iron, and with aluminum to make up to 100%, catalysts with an iron content of about 12.8 to 25% by weight (preferably) or about 14.2–25% by weight (particularly preferably) being obtained.

The alloy and the catalysts can be prepared by processes which are in themselves known, for example according to R. Schröter, Angewandte Chemie, 54, (1941), 229–234, B. M. Bogolowski and S. S. Kosakowa, "Skelettkatalysatoren in der organischem Chemie" ("Skeleton catalysts in organic Chemistry"), VEB Deutscher Verlag Berlin (1960), or according to Houben Weyl, Methoden der organischen Chemie (Methods of organic Chemistry), (1955), volume 4/2, page 171–175.

In general, to prepare the catalyst the comminuted alloy—dry or as an aqueous suspension—is treated with inorganic or organic bases in a manner which is in itself known, the aluminum being dissolved out, with the evolution of hydrogen, down to a residue of about 3 to 9% by weight. Aqueous sodium hydroxide solution with a concentration of about 10 to 30, preferably about 15 to 25% by weight is preferably used as the base. In general, the decomposition of the alloy is carried out at about 30° to 110° C., preferably at about 60° to 90° C. and particularly preferably at about 70° to 80° C. For the decomposition, the alloy is introduced into the aqueous sodium hydroxide solution at the temperature indicated. Conversely, however, the sodium hydroxide solution can also be added to an aqueous suspension of the alloy. The last-mentioned procedure is preferably used if the aluminum is to be only partially dissolved out.

After separating off the aluminate liquor, the catalyst is initially washed with sodium hydroxide solution and then with water until neutral. Both distilled water and water purified over an ion exchanger, as well as drinking water, if its purity is sufficient, can be used as the water.

The catalysts according to the invention can be used for the hydrogenation of the most diverse organic compounds, for which the catalysts of the Raney type are customarily employed (compare R. Schröter and B. M. Bogoslowski and S. S. Kosakowa see loc. cit.).

The formation of by-products, which is known in the case of Raney nickel catalysts, is greatly suppressed by adding iron. Thus, for example, during the hydrogenation of phenol the formation of cyclohexane is reduced by more than 2% and the formation of cyclopentanol is reduced to below the limits of detection. During the reduction of nitro compounds in methanol, the formation of N-alkyl derivatives, which is of great consequence especially at the higher temperatures of the industrial procedure (compare Houben-Weyl, volume 11/1 (1957), page 124 and 343), it also greatly reduced; the same applies to the suppression of the hydrogenation of the aromatic nucleus.

A surprising and unforeseeable effect is the same or greater activity of the catalysts according to the invention compared with customary Raney nickel catalysts. Since Raney iron is known as a catalyst of low activity (see R. Paul and G. Hilly, loc. cit.), an increase in the activity was in no way to be expected with additions of about 10 to 30% by weight of Fe to Raney nickel.

The observed increases in activity manifests itself, in particular, in the example of the reduction of 2,4/2,6-dinitrotoluene in methanol or isopropanol/water mixtures. It runs parallel with the decreasing tendency towards formation of by-products, in particular those from the N-alkylation reaction with the solvent.

Thus, for example, the catalyst according to the invention is significantly more active in methanol than the simple Raney nickel catalyst. In isopropanol/water, where only a very slight N-alkylation can be detected, the catalyst exhibits the greatest activity, that is to say in this solvent it permits the shortest reaction times—almost only half the reaction time required for the customary Raney nickel catalyst in methanol—, it being possible, at the same time, to keep the reaction temperatures exceptionally low, whilst the life of the catalyst is very high. In the case of the high run content with its dominating action, additions of further metals do not substantially alter the properties of the catalysts.

Thus, compared with the Raney nickel catalysts, the use of the catalyst according to the invention in methanol is a considerable improvement in the state of the art; a further improvement is achieved by the combination of the catalyst according to the invention ("RaNiFe") and an isopropanol/water mixture as the solvent. The isopropanol/water solvent is preferably the mixture with a content of about 80 to 85% by weight of isopropanol, which is close to the azeotrope.

When carrying out hydrogenation reactions, using the catalyst according to the invention, on an industrial scale, the advantages of the new catalyst become clear to a yet far greater extent. Thus, in the continuous hydrogenation of 2,4/2,6-dinitrotoluene, in addition to the increase in yields, in particular the amount of catalyst required, which is lower by more than 50% compared to the customary Raney catalysts, the feasible throughput, which is almost twice as high, and the enormous increase in working life are noteworthy. Together with the basic reduction in cost of the catalyst as a result of the low price of iron, the improvement in the process with respect to cost is considerable. Comparable improvements can also be observed in the industrial reduction of other nitro compounds.

For example, in the industrial production of p-phenetidine, the outstanding dechlorination of the chloronitro compound, present in the industrial starting material, in, at the same time, excellent yield, whereby in particular an improvement which is decisive for the further processing of the hydrogenation product is achieved, is an added further effect of the combination RaNiFe + isopropanol/water.

Since no metals which interfere with the working-up are present in the catalyst according to the invention, a further advantage is that the recycling of the metals also causes no difficulties.

In the following examples, the percentage data, unless otherwise indicated, are percent by weight.

By the term "RaNi" is meant a customary Raney nickel catalyst which has been prepared, analogously to Example 1 which follows, from an aluminium/nickel alloy with a nickel content of 30% by weight.

EXAMPLE 1

Preparation of the catalyst 100 parts by weight of an AlNiFe alloy having a composition of 50% of Al, 42.5% of Ni and 7.5% of Fe are slowly introduced in portions into 1,223 parts by weight of 20% strength by weight aqueous sodium hydroxide solution at 80° C. in the course of about 50 to 60 minutes, whilst stirring and cooling. In order to bring the reaction to completion, stirring is continued for a further 20 minutes at 80° C.

After allowing the catalyst to settle, the aluminate liquor is substantially decanted off. The catalyst is then treated with 122 parts by weight of 20% strength by weight NaOH for 15 minutes at 80° C., whilst stirring, and then washed with water at room temperature until the wash water is neutral, the catalyst being stirred up each time and, after allowing the catalyst to settle, the supernatent liquor being decanted off from the catalyst.

The catalyst is stored under water and contains 15% of iron, relative to the active metals Ni and Fe.

In the same manner, a catalyst containing 20% of iron can also be prepared from a starting alloy having a composition of 50% of Al, 40% of Ni and 10% of Fe.

EXAMPLE 2

Preparation of the catalyst

A Raney nickel/iron catalyst which contains 25% of iron, relative to the sum of the active metals, is prepared analogously to Example 1 from 100 parts by weight of an alloy of 71.4% by weight of Al, 21.4% by weight of Ni and 7.2% by weight of Fe and 1,745 parts by weight of 20% strength by weight NaOH.

The introduction of the alloy is carried out at 40° to 60° C. and the mixture is then stirred for 30 minutes at 80° C. in order to bring the reaction to completion.

Catalysts which contain 15% of iron, relative to the sum of the active metals, are prepared by the same method from alloys having contents of 70.7% of Al, 24.9% of Ni and 4.4% of Fe and 70.0% of Al, 25.5% of Ni and 4.5% of Fe. The introduction is carried out at 80° C.

EXAMPLE 3

Preparation of the catalyst

An Al/Ni/Fe alloy is prepared from 60 parts by weight of aluminium, 32 parts by weight of nickel and 8 parts by weight of iron and is comminuted.

1,400 parts by weight of 20% strength by weight sodium hydroxide solution are initially introduced into a stirred vessel, which is provided with heating and cooling and is blanketed with nitrogen, and are warmed to 80° C. 100 parts by weight of the comminuted Al/Ni/Fe alloy, under water, are then introduced via a gas-tight charging device, whilst stirring. During this process, hydrogen is formed and is led off. The internal temperature is kept at 80° C. with the aid of the cooling; time required: about 2 hours.

After the introduction has ended, the kettle is subsequently kept at 80° C. for a further 2 hours. Thereafter, the contents of the kettle are forced in a filter and the aluminate liquor is thereby separated off. The catalyst, which remains in the filter, is washed with 70 parts by weight of 20% strength by weight NaOH and then rinsed with water in a settling vessel. The catalyst is washed in the latter with, in each case, 220 parts by weight of water, by stirring up, settling and decanting, until the pH of the wash water has reached the value 8. The finished catalysts is stored under water and contains 20% of iron, relative to the sum of the active metals.

In the same manner, catalysts are prepared from alloys with a ratio of Al:Ni:Fe of 60:30:10; 60:34:6; 60:36:4 and 60:37.6:2.4, and these catalysts contain 25, 15, 10 and 6% of iron respectively, relative to the sum of the active metals.

EXAMPLE 4

Hydrogenation of phenol (A) Discontinuous hydrogenation

In each case, 200 g of phenol and 10 g of the catalyst (100%) mentioned in the table which follows are hydrogenated in a 0.7 l autoclave, with a stirrer and external electrical heating, at 230° C. and under a hydrogen pressure of 150 bars. In addition to the reaction time, the temperature at which the reaction begins (the so-called start temperature) is recorded. The hydrogenation product is examined by gas chromatography.

The next hydrogenation in the series tests is carried out with the used catalyst which remains in the autoclave and has settled and from which the hydrogenation product has been decanted off.

The number of re-employments of the catalyst is indicated in the table which follows, and also in the tables of the subsequent examples, in the column containing the data on the hydrogenation number, which accordingly indicates how many times the catalyst was employed in the series test.

The following results were achieved:

| Catalyst | Hydrogenation No | Reaction time minutes | Reaction start temperature °C. | Pressure bars | Analysis (without water) | | |
|---|---|---|---|---|---|---|---|
| | | | | | Cyclo-hexane | Other by-products | Cyclo-hexanol |
| (a) RaNi (for | 1 | 14 | 70–230 | 150 | 3.45 | 0.32 | 96.23 |
| comparison) | 2 | 12 | 86–230 | 150 | 2.57 | 0.37 | 97.04 |
| | 9 | 13 | 115–230 | 150 | 2.07 | 0.36 | 97.57 |
| (b) RaNiFe (15%) | 1 | 13 | 80–230 | 150 | 0.09 | 0.05 | 99.86 |
| according to | | | | | | | |
| Example 2 | 2 | 13 | 113–230 | 150 | 0.26 | 0.15 | 99.59 |
| 70.7% of Al | 5 | 12 | 118–230 | 150 | 0.23 | 0.15 | 99.62 |
| 24.9% of Ni | | | | | | | |
| 4.4% of Fe | | | | | | | |
| (c) RaNiFe (25%) | 1 | 14 | 89–230 | 150 | 0.06 | 0.04 | 99.90 |
| according to | | | | | | | |
| Example 2 | 2 | 13 | 128–230 | 150 | 0.09 | 0.07 | 99.84 |
| 71.4% of Al | 7 | 12 | 130–230 | 150 | 0.10 | 0.11 | 99.79 |
| 21.4% of Ni | | | | | | | |
| 7.2% of Fe | | | | | | | |

1–2% of cyclohexane are formed under the same conditions with a Raney nickel/cobalt catalyst (25% of Co). As the results show, the cheaper RaNiFe catalysts require the same reaction time but give a yield which is improved by more than 2%.

(B) Continuous hydrogenation

The advantages of the new catalysts become clear, in particular, in the industrial hydrogenation of phenol. In the continuous sump phase hydrogenation of phenol in a reaction tube, the procedure of which is described in detail in Example 11 which follows, not only are the yields greatly increased and the cyclopentanol, which interferes with further processing, eliminated, but, in particular, the amount of catalyst required is also reduced, whereby the process becomes more economical.

| Average analysis in % | RaNi (for comparison) | RaNiFe (20%) based on the alloy 60/Al, 32/Ni and 8/Fe according to Ex. 3 |
|---|---|---|
| Cyclohexane | 3.160 | 0.58 |
| Unknown | 0.0005 | — |
| Benzene | 0.010 | 0.04 |
| Water | 0.718 | 0.32 |
| Cyclopentanone | 0.003 | — |
| Cyclopentanol | 0.014 | — |
| Cyclohexanone | 0.144 | 0.03 |
| Cyclohexanol | 95.510 | 98.87 |
| Unknown constituents | 0.008 | — |
| " | 0.003 | — |
| Dicyclohexyl ether | 0.381 | 0.09 |
| Phenol | 0.044 | 0.07 |
| Amount of catalyst required for 100 kg of crude cyclohexanol | 0.095 kg | 0.34 kg |

EXAMPLE 5

Hydrogenation of m-nitrotoluene

In each case 100 g of m-nitrotoluene in 200 g of methanol and 10 g of catalyst (100% pure) having the composition given in the table which follows are hydrogenated in a 0.7 l stirred autoclave at 100° C. and under a hydrogen pressure of 100 bars.

The solution of the finished product, which is decanted off, is analysed by gas chromatography.

The used catalyst which has settled out is used further in the next test.

The new catalyst produces less by-products during an approximately equal reaction time, in particular when re-used more frequently.

| Catalyst | Hydrogenation No. | Reaction time minutes | Reaction start temperature °C. | Pressure bars | Analysis Cyclohexylamine | N-alkyl compound |
|---|---|---|---|---|---|---|
| RaNi (for comparison) | 1 | 14 | 25–100 | 100 | 0.50 | 0.19 |
|  | 2 | 14 | 32–100 | 100 | 0.21 | 0.30 |
|  | 5 | 28 | 75–100 | 100 | 0.12 | 0.47 |
|  | 7 | 29 | 78–100 | 100 | 0.23 | 0.41 |
| RaNiFe 20% according to Example 3 from an alloy containing 60% of Al 32% of Ni 8% of Fe | 1 | 14 | 38–100 | 100 | 0.05 | 0.05 |
|  | 2 | 23 | 48–100 | 100 | <0.01 | 0.07 |
|  | 5 | 31 | 58–100 | 100 | <0.01 | 0.06 |
|  | 7 | 34 | 75–100 | 100 | <0.01 | 0.05 |

EXAMPLE 6

Hydrogenation of nitrobenzene

When tested the same as in Example 5—100 g of nitrobenzene, 200 g of methanol and 10 g of catalyst (100%)—the new catalyst also produces less by-products here:

EXAMPLE 7

Hydrogenation of p-nitrophenetol

The testing of the new catalyst—100 g of p-nitrophenetol, 200 g of methanol or isopropanol/water (85:15, as the solvent, 1 ml of 20% strength KOH and 10 g of catalyst—gave the following result: in methanol, the formation of N-alkyl compounds was greatly reduced, whilst the rate of reaction was the same. In isopropanol/water (85:15), in addition to the boosting of this effect, in particular the lower start temperature and the almost complete dechlorination of the chloroaniline, which originates from the chloronitrobenzene (about 0.5 to 0.6%) contained in the p-nitrophenetol, are conspicuous.

| Catalyst | Hydrogenation No. | Reaction time minutes | Reaction start temperature °C. | Pressure bars | Toluidine | N-alkyl compound | Other by-products |
|---|---|---|---|---|---|---|---|
| (a) RaNi (for comparison) | 1 | 13 | 25–100 | 100 | 99.36 | 0.54 | 0.10 |
|  | 2 | 15 | 31–100 | 100 | 99.02 | 0.54 | 0.04 |
|  | 5 | 17 | 68–100 | 100 | 98.68 | 1.23 | 0.09 |
|  | 10 | 27 | 77–100 | 100 | 98.86 | 1.08 | 0.06 |
| (b) RaNiFe 25% according to Example 3 from an alloy containing 60% of Al 32% of Ni 8% of Fe | 1 | 10 | 25–100 | 100 | 99.54 | 0.42 | 0.04 |
|  | 2 | 15 | 25–100 | 100 | 99.49 | 0.50 | 0.01 |
|  | 5 | 23 | 62–100 | 100 | 99.32 | 0.68 | — |
|  | 10 | 30 | 77–100 | 100 | 99.55 | 0.45 | — |

| Catalyst | Solvent | Hydrogenation No. | Reaction time minutes | Reaction start temperature °C. | Pressure bars | Chloroaniline | N-alkyl compound |
|---|---|---|---|---|---|---|---|
| (a) RaNi (for comparison) | Methanol | 1 | 5 | 25–100 | 100 | 0.05 | 0.15 |
|  |  | 2 | 6 | 44–100 | 100 | 0.41 | 1.39 |
|  |  | 3 | 8 | 60–100 | 100 | 0.35 | 1.56 |
|  |  | 4 | 8 | 72–100 | 100 | 0.37 | 2.55 |
| (b) RaNiFe (20%) according to Example 3 from an alloy containing 60% of Al 32% of Ni 8% of Fe | Methanol | 1 | 8 | 25–100 | 100 | 0.01 | 0.15 |
|  |  | 2 | 8 | 38–100 | 100 | 0.19 | 0.46 |
|  |  | 3 | 8 | 55–100 | 100 | 0.43 | 0.51 |
|  |  | 4 | 8 | 67–100 | 100 | 0.51 | 0.36 |
| (c) RaNiFe (15%) according to | Isopropanol/water 85:15 | 1 | 9 | 25–100 | 100 | 0.005 | 0.04 |

| Catalyst | Solvent | Hydrogenation No. | Reaction time minutes | Reaction start temperature °C. | Pressure bars | Analysis Chloro-aniline | Analysis N-alkyl compound |
|---|---|---|---|---|---|---|---|
| Example 2 from an alloy containing 70% of Al 25.5% of Ni 4.5% of Fe | | 2 | 9 | 39-100 | 100 | 0.005 | 0.03 |
| | | 3 | 9 | 40-100 | 100 | 0.005 | 0.03 |
| | | 4 | 9 | 40-100 | 100 | 0.005 | 0.03 |

EXAMPLE 8

Hydrogenation of a 2,4/2,6-dinitrotoluene mixture (65/35)

In each 80 g of a 2,4/2,6-dinitrotoluene mixture (65% of the 2,4 isomer and 35% of the 2,6 isomer) in 240 g of methanol of isopropanol/water (85:15) are hydrogenated in a 0.7 l stirred autoclave, with external electrical heating, at 100° C. and under a hydrogen pressure of 100 bars, the following results being obtained:

| Catalyst | Solvent | Hydrogenation No. | Reaction time minutes | Reaction start temperature °C. | Pressure bars |
|---|---|---|---|---|---|
| (a) RaNi (for comparison) | Methanol | 1 | 19 | 25-100 | 100 |
| | | 2 | 33 | 25-100 | 100 |
| | | 5 | 36 | 65-100 | 100 |
| | | 10 | 36 | 76-100 | 100 |
| | | 15 | 41 | 78-100 | 100 |
| (b) RaNi (for comparison) | Isopropanol/water | 1 | 19 | 25-100 | 100 |
| | | 2 | 21 | 25-100 | 100 |
| | | 5 | 23 | 38-100 | 100 |
| | | 10 | 25 | 40-100 | 100 |
| | | 15 | 25 | 40-100 | 100 |
| (c) RaNiFe 15% according to Ex. 3 from an alloy 60% of Al 34% of Ni 6% of Fe | Methanol | 1 | 12 | 25-100 | 100 |
| | | 2 | 14 | 38-100 | 100 |
| | | 5 | 21 | 48-100 | 100 |
| | | 7 | 21 | 55-100 | 100 |
| (d) RaNiFe 15% according to Ex. 3 from an alloy 60% of Al 34% of Ni 6% of Fe | Isopropanol/water | 1 | 14 | 25-100 | 100 |
| | | 2 | 17 | 35-100 | 100 |
| | | 5 | 17 | 35-100 | 100 |
| | | 10 | 18 | 38-100 | 100 |
| | | 15 | 19 | 39-100 | 100 |

The content of N-alkyl compounds is 0.1 to 0.15% for the hydrogenation in methanol and 0.01% for the hydrogenation in isopropanol/water.

Compared with RaNi in methanol, the reaction time using the Raney nickel/iron catalyst in isopropanol/water, particularly when used several times, is reduced by half and, in addition, the start temperature falls by almost 40° C.

EXAMPLE 9

Hydrogenation of a 2,4/2,6-dinitrotoluene mixture (65/35) on a Raney nickel/iron catalyst containing only 6% by weight of iron (for comparison)

The procedure followed was as in Example 6, the following results having been obtained:

| Catalyst | Solvent | Hydrogenation No. | Reaction time minutes | Reaction start temperature °C. | Pressure bars |
|---|---|---|---|---|---|
| (a) RaNiFe 6% according to Ex. 3 from an alloy 60% of Al 37.6% of Ni 2.4% of Fe | Methanol | 1 | 14 | 25-100 | 100 |
| | | 2 | 22 | 25-100 | 100 |
| | | 5 | 23 | 47-100 | 100 |
| | | 10 | 31 | 62-100 | 100 |
| (b) RaNiFe 6% according to Ex. 3 from an alloy 60% of Al 37.6% of Ni 2.4% of Fe | Isopropanol/water | 1 | 15 | 32-100 | 100 |
| | | 2 | 21 | 35-100 | 100 |
| | | 5 | 22 | 38-100 | 100 |
| | | 10 | 25 | 44-100 | 100 |

Although the Raney nickel/iron catalyst containing 6% of Fe is again more active in isopropanol/water, it does not achieve the reaction times of the Raney nickel/iron catalyst according to the invention containing 15% of iron. A determination of the residue by laboratory distillation gave a residue of 4.4% in the case of methanol and 3.4% in the case of isopropanol/water.

A comparison of a Raney nickel/iron catalyst according to the invention containing 10% by weight of iron with a Raney nickel/iron/chromium catalyst containing 5% by weight of iron and 5% by weight of chromium—both catalysts contain 10% by weight of foreign metals—shows that the chromium-containing catalyst does not completely hydrogenate the dinitro compound, since a residual nitro content of 0.25 to 0.38% was determined.

EXAMPLE 10

Hydrogenation of a 2,4/2,6-dinitrotoluene mixture (65/35)

Catalysts with a higher iron content obtained from alloys with a different aluminium content also prove to be more active than normal Raney nickel. The following catalysts were tested:

| Catalyst | Solvent | Hydrogenation No. | Reaction time minutes | Reaction start temperature °C. | Pressure bars |
|---|---|---|---|---|---|
| (a) RaNiFe (20%) according to Ex. 3 | Methanol | 1 | 15 | 38-100 | 100 |
| | | 2 | 16 | 38-100 | 100 |

-continued

| Catalyst | Solvent | Hydrogenation No. | Reaction time minutes | Reaction start temperature °C. | Pressure bars |
|---|---|---|---|---|---|
| from an alloy containing 60% of Al 32% of Ni 8% of Fe | | 3<br>4<br>5 | 16<br>16<br>17 | 50-100<br>55-100<br>55-100 | 100<br>100<br>100 |
| (b) RaNiFe (25%) according to Ex. 3 | Methanol | 1<br>2 | 15<br>16 | 55-100<br>42-100 | 100<br>100 |
| from an alloy containing 60% of Al 30% of Ni 10% of Fe | | 3<br>4<br>5 | 16<br>16<br>16 | 42-100<br>45-100<br>50-100 | 100<br>100<br>100 |
| (c) RaNiFe (25%) according to Ex. 1 | Methanol | 1<br>2 | 19<br>13 | 70-100<br>44-100 | 100<br>100 |
| from an alloy containing 70% of Al 22.5% of Ni 7.5% of Fe | | 3<br>4 | 15<br>16 | 38-100<br>38-100 | 100<br>100 |
| (d) RaNiFe (20%) according to Ex. 2 | Methanol | 1<br>2 | 14<br>13 | 52-100<br>48-100 | 100<br>100 |
| from an alloy containing 50% of Al 40% of Ni 10% of Fe | | 3<br>4 | 13<br>15 | 48-100<br>48-100 | 100<br>100 |
| (e) RaNiFe (15%) according to Ex. 2 | Methanol | 1<br>2 | 13<br>13 | 38-100<br>41-100 | 100<br>100 |
| from an alloy containing 50% of Al 42.5% of Ni 7.5% of Fe | | | | | |
| (f) RaNiFeMo according to Ex. 3 | Methanol | 1<br>2 | 14<br>14 | 55-100<br>55-100 | 100<br>100 |
| from an alloy containing 59% of Al 32% of Ni 8% of Fe 1% of Mo | | 3 | 17 | 71-100 | 100 |

EXAMPLE 11

Continuous hydrogenation of a 2,4/2,6-dinitrotoluene mixture (65:35) "DNT"

The continuous sump phase hydrogenation apparatus used, which is represented in FIG. 1, consists of four reactors (8 to 11) connected in series, which are provided with cooling tubes in order to remove the heat of reaction, and also of the product cooler (12), the separators (13, 14) and the gas circulation pump (15), with the aid of which a hydrogen circulation is produced.

The hydrogenation mixture is continuously formed in the mixing kettle (6) from dinitrotoluene (1), the solvent (2), the fresh catalyst (3)—suspended in the solvent— and the concentrated circulating contact catalyst (4) coming from the filter (17) and suspended in the solution of the finished product. The hydrogenation mixture is continuously pumped into the reactors (8 to 10) by means of the high pressure pumps (7), and is reacted there with hydrogen (5), which is fed into the reactor (8) together with the circulating hydrogen. After cooling in the cooler (12) and after separating in the separators (13, 14), the solution of the finished product leaving the reactors enters the let-down kettle (16). The gas phase of the separator—the excess of hydrogen—is recycled again to the initial reactor (8) by means of the circulation pump (15).

The solution of the finished product with the suspended catalyst from container (16) is separated in the filter (17) into the filtrate, which passes to (18) for working up, and into the recycled product (4), which brings the circulating catalyst back to the mixing kettle. A proportion of the catalyst suspension—corresponding to the amount of fresh catalyst added—can be withdrawn via a discharge device (18) and worked up.

The industrial advantages, the advantages with respect to quality and in particular the advantages of a lowering in cost in employing Raney nickel/iron catalysts with isopropanol/water as the solvent can be clearly seen from the following comparison of the results of tests carried out over a period of several years.

| Catalyst: | RaNi (for comparsion) | RaNiFe (15%) according to Example 3 from an alloy containing 60% of Al 34% of Ni 6% of Fe |
|---|---|---|
| Solvent: | Methanol | Isopropanol/water (85:15) |
| Installation pressure (bars) | 100 | 100 |
| Minimum operating temperature required in use | 170-185 | 155-170 |
| Maximum possible throughput (t of DNT/hour) | 3-3.5 | 5-6 |
| Life, that is to say maximum time between two necessary purifications | 3-4 weeks | over 2 years |
| Quality: | | |
| Content of N-alkyl compounds (%) | 0.3-0.6 | <0.05 |
| of residue | 0.9 | <0.5 |
| Catalyst consumption per kg of DNT (%) | ≧0.1 | ≦0.04 |

Comparable results are achieved if a Raney nickel/iron catalyst with an iron content of 20%, relative to the active metals, and prepared from an alloy according to Example 3 with a content of 60% of Al, 32% of Ni and 8% of Fe is employed.

The results achieved when a 2,4/2,6-dinitrotoluene mixture (65/35) is employed are also achieved with 2,4-dinitrotoluene and the 2,4/2,6-dinitrotoluene mixture (80/20) which, as industrial material, also contains other isomers.

The used catalyst which is discharged from the continuous sump phase hydrogenation of dinitrotoluene mixtures still has an activity such that it can be re-employed with good results, alone or mixed with small proportions of unused catalyst, for the hydrogenation of other nitro compounds, for example nitrotoluene.

EXAMPLE 12

Continuous hydrogenation of p-nitrophenetole and m-nitrotoluene

The following improvement is obtained with RaNiFe in the continuous hydrogenation of p-nitrophenetole in the apparatus described in Example 11:

| Catalyst | Solvent | % of chloroaniline | % of N-alkyl compounds |
|---|---|---|---|
| RaNi (for | Methanol | 0.01 | 0.3-0.7 |

-continued

| Catalyst | Solvent | % of chloroaniline | % of N-alkyl compounds |
|---|---|---|---|
| comparsion) RaNiFe (15%) according to Example 3 from an alloy containing 60% of Al 34% of Ni 6% of Fe | Isopropanol/ water | 0.001-0.003 | 0.15-0.2 |

In the continuous hydrogenation of m-nitrotoluene, carried out in the same manner, the content of N-alkyl products can be lowered by 0.2 to 0.3% to ≦0.1%. In both cases, the throughput is increased by more than 50%.

What is claimed is:

1. In a process for the hydrogenation of an organic aromatic nitro compound which comprises hydrogenating said organic compound in the presence of a Raney nickel catalyst, the improvement which comprises using, as the Raney nickel catalyst, one which contains about 12.8 to 25% by weight of iron, relative to the sum of the active components nickel and iron.

2. The process of claim 1 wherein said Raney nickel/iron catalyst contains about 14.2 to 25% by weight of iron, relative to the sum of the active components nickel and iron.

3. A process of claim 1 wherein the aromatic nitro compound is an aromatic mononitro or dinitro compound.

* * * * *